(12) United States Patent
Gramnäs

(10) Patent No.: US 8,721,736 B2
(45) Date of Patent: May 13, 2014

(54) DAMPING DEVICE FOR A PROSTHESIS

(75) Inventor: Finn Gramnäs, Kinna (SE)

(73) Assignee: Ossur HF, Reykjavik (IS)

( * ) Notice: Subject to any disclaimer, the term of this patent is extended or adjusted under 35 U.S.C. 154(b) by 1699 days.

(21) Appl. No.: 11/795,138

(22) PCT Filed: Jan. 13, 2006

(86) PCT No.: PCT/SE2006/000056
§ 371 (c)(1),
(2), (4) Date: Sep. 12, 2007

(87) PCT Pub. No.: WO2006/075959
PCT Pub. Date: Jul. 20, 2006

(65) Prior Publication Data
US 2008/0140222 A1   Jun. 12, 2008

(30) Foreign Application Priority Data
Jan. 13, 2005   (SE) ....................... 0500098

(51) Int. Cl.
*A61F 2/64* (2006.01)
(52) U.S. Cl.
USPC ................................. 623/43; 623/39; 623/35
(58) Field of Classification Search
USPC ..................................................... 623/38, 43
See application file for complete search history.

(56) References Cited

U.S. PATENT DOCUMENTS

| | | | | |
|---|---|---|---|---|
| 4,005,496 A | * | 2/1977 | Wilkes | 623/44 |
| 4,370,761 A | * | 2/1983 | Serri | 623/43 |
| 4,883,493 A | | 11/1989 | Martel et al. | |
| 5,545,232 A | * | 8/1996 | Van de Veen | 623/39 |
| 5,904,721 A | * | 5/1999 | Henry et al. | 623/26 |
| 6,214,056 B1 | | 4/2001 | Wilkinson | |
| 6,302,918 B1 | | 10/2001 | Gramnäs | |
| 2004/0068325 A1 | | 4/2004 | Phillips et al. | |

FOREIGN PATENT DOCUMENTS

| | | |
|---|---|---|
| DE | 197 09 006 A1 | 9/1998 |
| JP | 2000333976 | 12/2000 |
| JP | 2002235785 | 8/2002 |

* cited by examiner

*Primary Examiner* — Bruce E Snow
*Assistant Examiner* — Melissa Hoban
(74) *Attorney, Agent, or Firm* — Workman Nydegger

(57) ABSTRACT

A damping device (1) for a prosthesis, comprising a first member (2) for connection to a first component, a second member (3) for connection to another component, and a means (4) for coupling together the first member and the second member and for relative displacement of the first member and the second member. A damping element (5) is arranged to counteract a relative displacement between the first member (2) and the second member (3) when loading the damping device (1). The coupling means 4 comprises at least two linkage arms (6, 7), both being pivotally arranged in relation to the first member (2) and the second member (3). The linkage arms (6, 7) are arranged at different positions with respect to a main damping direction (8) of the damping device for substantially maintaining the relative orientations of the first member (2) and the second member (3) when the first member and the second member are displaced in relation to each other, during pivoting of the linkage arms (6, 7) and exertion of influence on the damping element (5).

11 Claims, 8 Drawing Sheets

US 8,721,736 B2

DAMPING DEVICE FOR A PROSTHESIS

FIELD OF THE INVENTION

The present invention relates to a damping device for a prosthesis in accordance with the preamble of claim 1.

BACKGROUND OF THE INVENTION

The present invention is applicable to different types of prostheses, preferably leg prostheses, but for illustrative, but not limiting purposes, it will be described in the following how the invention can be utilised in order to create a damping device for damping in a vertical direction. When damping, it is often desirable to maintain the relative orientation between the components to which the damping device is connected during the damping phase. For leg prostheses, this can imply that it is desired to maintain the angle between the lower leg and the foot blade during vertical damping.

Leg prostheses according to prior art can be provided with a shock-absorbing action for absorbing a vertical load during foot strike. Damping in a vertical direction is particularly desirable in extreme situations, for example when a user steps down from a kerb, gets off a bus, descends a staircase, or the like. For this purpose, the lower leg member usually exhibits a so-called axial damping device, being arranged in the lower leg itself. The damping device can include two overlapping tubes, which can be displaced in relation to each other in an axial direction when loading the prosthesis, and a spring, which is arranged to counteract this movement. One disadvantage with these prostheses, however, is their relatively large mounting length.

Leg prostheses of this type are often useless for persons who, for example, are amputated relatively far below the knee joint, since these leg prostheses due to the integrated damping device have a mounting length which is too large. If the leg prosthesis has a mounting length, i.e. a distance from the underside of the foot blade to the point of attachment to the leg, being larger than the corresponding amputated portion, the prosthesis is out of the question for that person.

OBJECT OF THE INVENTION AND SUMMARY OF THE INVENTION

It is an object of the invention to provide a damping device for a prosthesis, preferably for damping in a vertical direction, wherein said damping device can exhibit a relatively small mounting length, at the same time as the angle between, for example, a foot blade and a lower leg can be essentially maintained during the damping phase.

The above-mentioned object is achieved by means of a damping device according to claim 1.

Since the coupling means comprises at least two linkage arms, both being pivotally arranged in relation to the first member and the second member, wherein the linkage arms are arranged at different positions with respect to a main damping direction of the damping device for substantially maintaining the relative orientations of the first member and the second member when loading the damping device and when the first member and the second member are displaced in relation to each other during pivoting of the linkage arms and exertion of influence on the damping element, the angle between for example a lower leg being connected to the first member and a foot blade being connected to the second member can be substantially maintained during the damping phase. At the same time, it is possible to arrange the damping element at a position between the first member and the second member, implying that the damping device can be designed with a relatively small extension length in the damping direction with the purpose of minimizing the mounting length of a prosthesis being provided with the damping device according to the invention.

Furthermore, the damping device according to the invention provides a possibility to integrate a number of functions into a prosthesis, for example into an ankle joint, while maintaining a small mounting length.

BRIEF DESCRIPTION OF THE DRAWINGS

A closer description of exemplary embodiments of the invention will follow below with reference to the attached drawings.

In the drawings.

DETAILED DESCRIPTION OF PREFERRED EMBODIMENTS OF THE INVENTION

Figure 1:
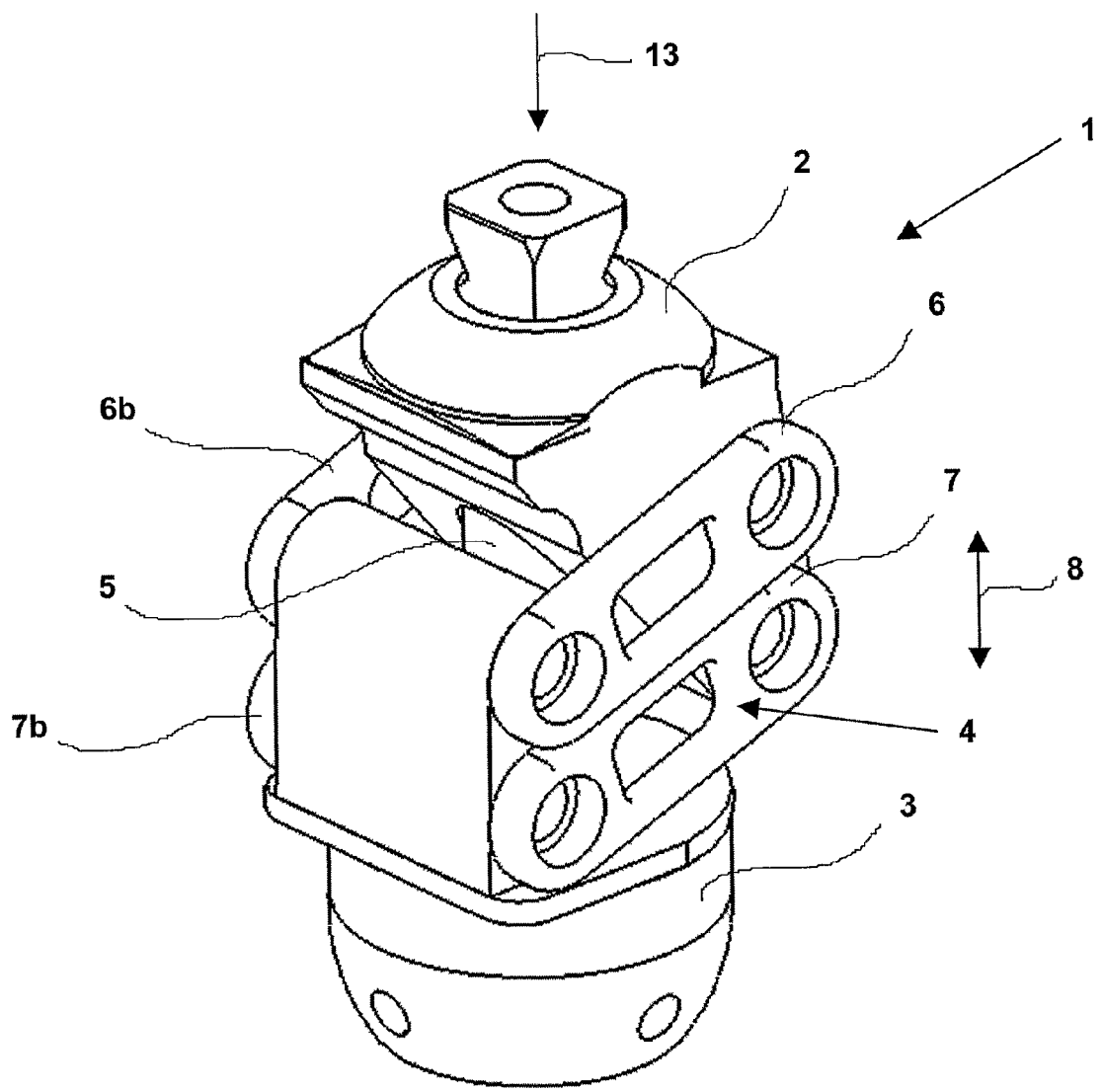
FIG. 1 is a perspective view of a damping device according to the invention.
Figure 2A:
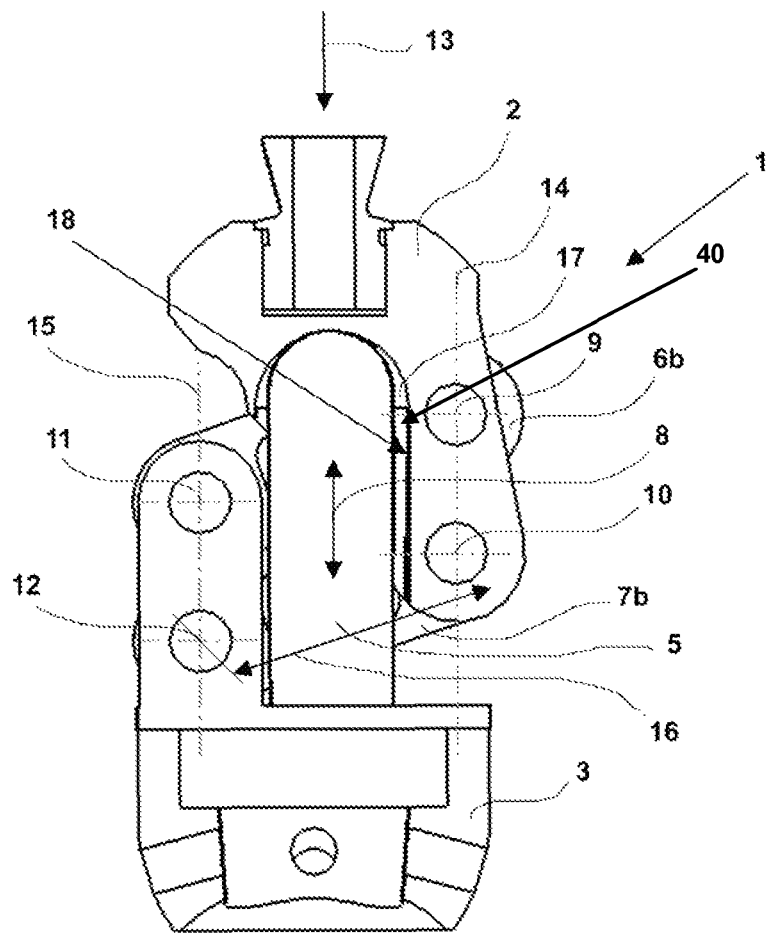
FIG. 2a is a sectional side view of the damping device illustrated in FIG. 1.

In a perspective view, FIG. 1 illustrates a damping device 1 for a prosthesis according to the invention, and FIG. 2a shows the damping device 1 in a sectional side view. The damping device 1 comprises a first member 2 for connection to a first component, such as a leg or a prosthetic member, a second member 3 for connection to another component, such as a leg or a prosthetic member, and a means 4 for coupling together the first member 2 and the second member 3 and for relative displacement of the first member 2 and the second member 3. Furthermore, the damping device 1 exhibits a damping element 5, which is arranged to counteract a relative displacement between the first member 2 and the second member 3 when loading the damping device 1. The coupling member 4 includes at least two, preferably parallel, linkage arms 6, 7, both being pivotally arranged in relation to the first member 2 and the second member 3. The linkage arms 6, 7 are arranged at different positions with respect to the main damping direction 8 of the damping device 1 for substantially maintaining the relative orientations of the first member 2 and the second member 3 when loading the damping device 1, when the first member 2 and the second member 3 are displaced in relation to each other during pivoting of the linkage arms 6, 7 and exertion of influence on the damping element 5.

The term "exertion of influence on the damping element" encompasses the cases that the damping element 5 is either compressed or extended. Both damping elements with the property of counteracting a movement by means of the damping element being compressed during damping, and such counteracting a movement during extending the damping element, could be utilised in the damping device according to the invention. Furthermore, the damping element can be arranged such that damping is obtained during a relative displacement of the first and the second member either in a direction towards each other or in a direction away from each other. Preferably, however, a damping element 5 providing damping when it is compressed, by means of the first 2 and the second member 3 being displaced towards each other substantially in parallel with the main damping direction 8, is utilised.

Although the invention is exemplified by an embodiment where the coupling means 4 includes two sets of linkage arms, each including two of said linkage arms 6, 7 and 6b, 7b, respectively (one upper, 6 and 6b, respectively, and one lower, 7 and 7b, respectively, linkage arm in the illustrated examples), it should be pointed out that, within the scope of the invention, there is a possibility to utilise other linkage arm systems. Once the invention has been disclosed, a person skilled in the art should be able to develop other designs with different sets of cooperating linkage arms, including two, three or several linkage arms, enabling the angle between the first member and second member of the damping device to be substantially maintained during the damping phase. In certain embodiments of the invention, one or several of the linkage arms could be pivotally coupled to the first member and/or the second member, not by means of direct coupling but via one or several of the other linkage arms.

Furthermore, its should be pointed out that the size and design of the first member 2 and the second member 3 can be adapted to the components to which the damping device 1 is intended to be connected. This implies that the first 2 and the second member 3, in certain cases, can include smaller attachment or coupling devices and that they, in other cases, can constitute substantially the entire or a larger part of the prosthesis. The first 2 and the second member 3 can be detachably connectable to the connecting components, or they can be fixedly arranged in the connecting components or integrally manufactured with these so that only the coupling means can be disassembled when disassembling.

The coupling means 4 comprises at least said two linkage arms 6, 7, both being pivotally arranged in relation to the upper member 2 and the lower member 3. In the embodiment illustrated in FIGS. 1 and 2a, each of said two linkage arms 6, 7 has a geometrical axis of rotation 9, 10 for relative pivoting of the link and the first member 2, on one hand, and a geometrical axis of rotation 11, 12 for relative pivoting of the link and the second member 3, on the other hand. Furthermore, the linkage arms 6, 7 are arranged substantially straight above each other, since the damping direction 8 is substantially vertical in the illustrated embodiments. This implies that one of the linkage arms 6 is arranged above the other linkage arm 7, for maintaining the relative orientations of the first member 2 and the second member 3 when loading and damping substantially in the vertical direction 13. Accordingly, the lower linkage arm 7 is pivotally coupled to the second member 3, for pivoting about a lower geometrical axis of rotation 12, and pivotally coupled to the first member 2, for pivoting about an upper geometrical axis of rotation 10. Accordingly, in the same way, the upper linkage arm 6 is pivotally coupled to the second member 3, for pivoting about a lower geometrical axis of rotation 11, and pivotally coupled to the first member 2, for pivoting about an upper geometrical axis of rotation 9. All axes of rotation are substantially parallel and, in the example, substantially perpendicular to the damping direction 8, which in this case means that they are substantially horizontally located.

Preferably, the geometrical axes of rotation 9, 10, about which the linkage arms 6, 7 and the first member 2 can be pivoted in relation to each other, are arranged at different positions along a geometrical line 14 being substantially parallel to the main damping direction 8. Furthermore, the geometrical axes of rotation 11, 12, about which the linkage arms 6, 7 and the second member 3 can be pivoted in relation to each other, preferably are arranged at different positions along a second geometrical line 15 being substantially parallel to the main damping direction 8. In the illustrated example, the damping direction 8 and the vertical direction 13 are substantially coinciding with each other, and the two linkage arms 6, 7 are substantially of the same length and arranged substantially in parallel and arranged substantially adjacent to each other. The length of a linkage arm 7 refers to the distance 16 between the axes of rotation 10, 12, about which the linkage arm 7 can be pivoted in relation to the first member 3 and the second member 2. Accordingly, the effective length of the respective linkage arm is defined by the distance between the lower and the upper axis of rotation of the linkage arm in question. In order to increase the stability of the damping device 1, an additional set of linkage arms 6b, 7b can be arranged in parallel to the lower linkage arm and the upper linkage arm. In the embodiment illustrated in FIGS. 1 and 2a, the damping device comprises two upper linkage arms 6, 6b and two lower linkage arms 7, 7b, being located on different sides of the damping element 5.

Preferably, the damping element 5 is arranged between the first member 2 and the second member 3, but it could also be arranged for example between a component of the coupling means and the first member or the second member. The damping element 5 can be attached to one of the first and the second member, or be loosely arranged in relation to the other of the first and the second member, or be loosely arranged in relation to both the first and the second member. At least one of the first member and the second member can be designed with a recess 17 for accommodating the damping element 5. Such a recess 17 means that a certain guiding of the damping element 5 is obtained and, furthermore, a relatively elongated damping element 5 can be used, without adversely influencing the distance between the first 2 and the second member 3. In other words, the damping element 5 can be considerably longer than the maximum damping stroke, being determined by the hardness of the damping element 5 and/or by the distance between the first member 2 and the second member 3 or by another stop function limiting the displacement of the first 2 and the second 3 member in relation to each other.

Figure 2B:
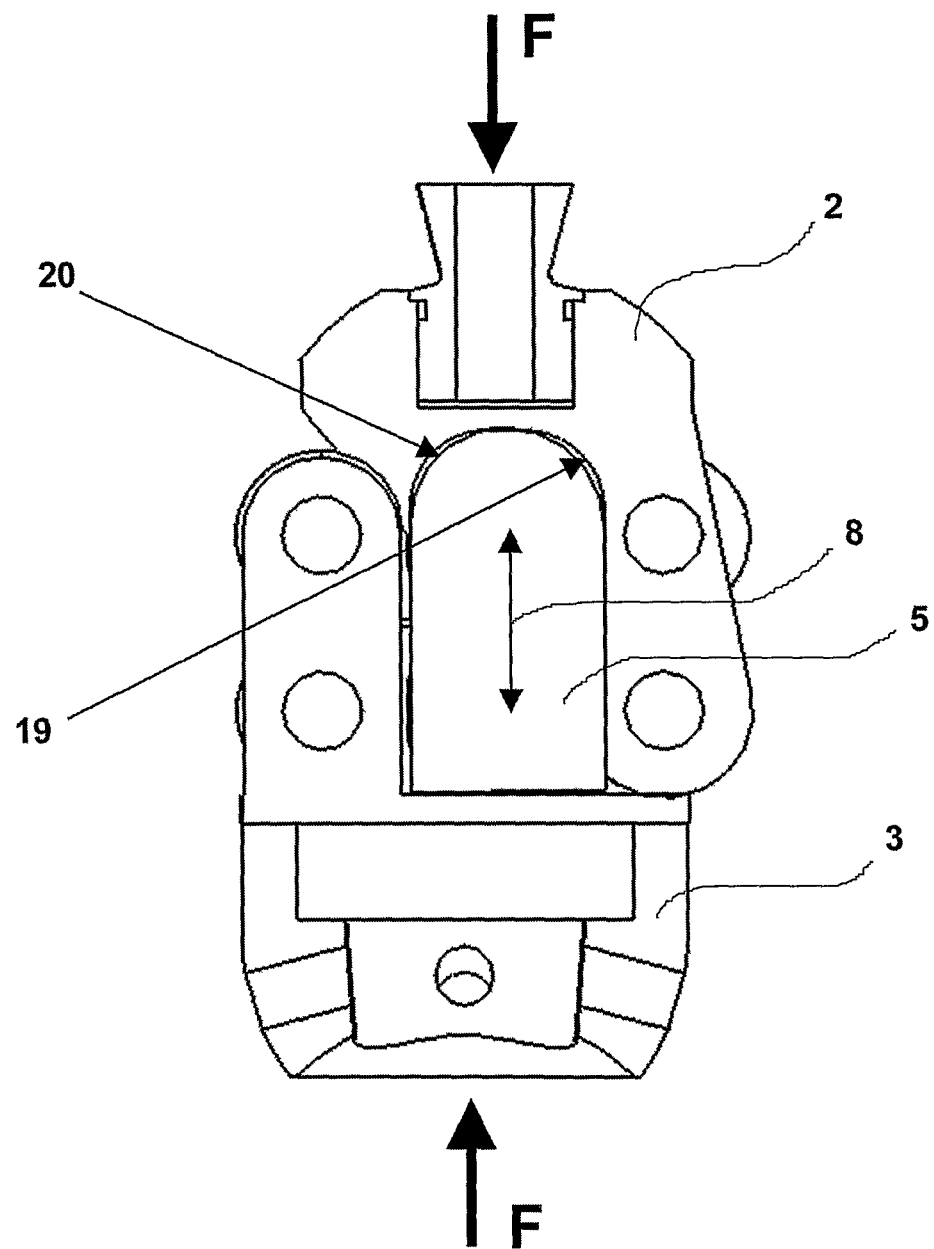
FIG. 2b is a view corresponding to FIG. 2a, showing the damping device in a loaded condition.

The recess 17 and the damping element 5 can be designed such that a play 40 is present between the limiting surface 18 of the recess 17 and the damping element 5 in one or more directions being substantially perpendicular to the main damping direction 8. This enables a certain relative displacement of this member 2, being provided with the recess 17, and the damping element 5, something which can facilitate the damping movement in case the actual damping direction is not completely rectilinear and/or the damping element 5, during compression in the damping direction 8, expands in directions which are substantially perpendicular in relation to the damping direction 8. In FIG. 2b, it is illustrated how the damping element 5 has been compressed in the damping direction 8 and has expanded in directions being perpendicular to the damping direction 8, said expansion being enabled by the recess 17 in the first member 2. The recess 17, preferably having a circular cross-section, conveniently has a larger diameter than the damping element 5. Furthermore, the bottom surface 19 of the recess 17 can be spherical and the damping element 5 can also be designed with a corresponding spherical surface 20 which, at least in an unloaded condition, preferably has a slightly smaller radius than the bottom surface 19 of the recess, thereby facilitating a relative movement between the first member 2 and the damping element 5 during relative displacement of the first member 2 and the second member 3.

The damping element 5 can be made of rubber or of another suitable resilient material. Naturally, there is a possibility to use different types of damping elements of different materials, dimensions and/or with different hardness, in order to vary the damping characteristics of the damping device.

Figure 3A:
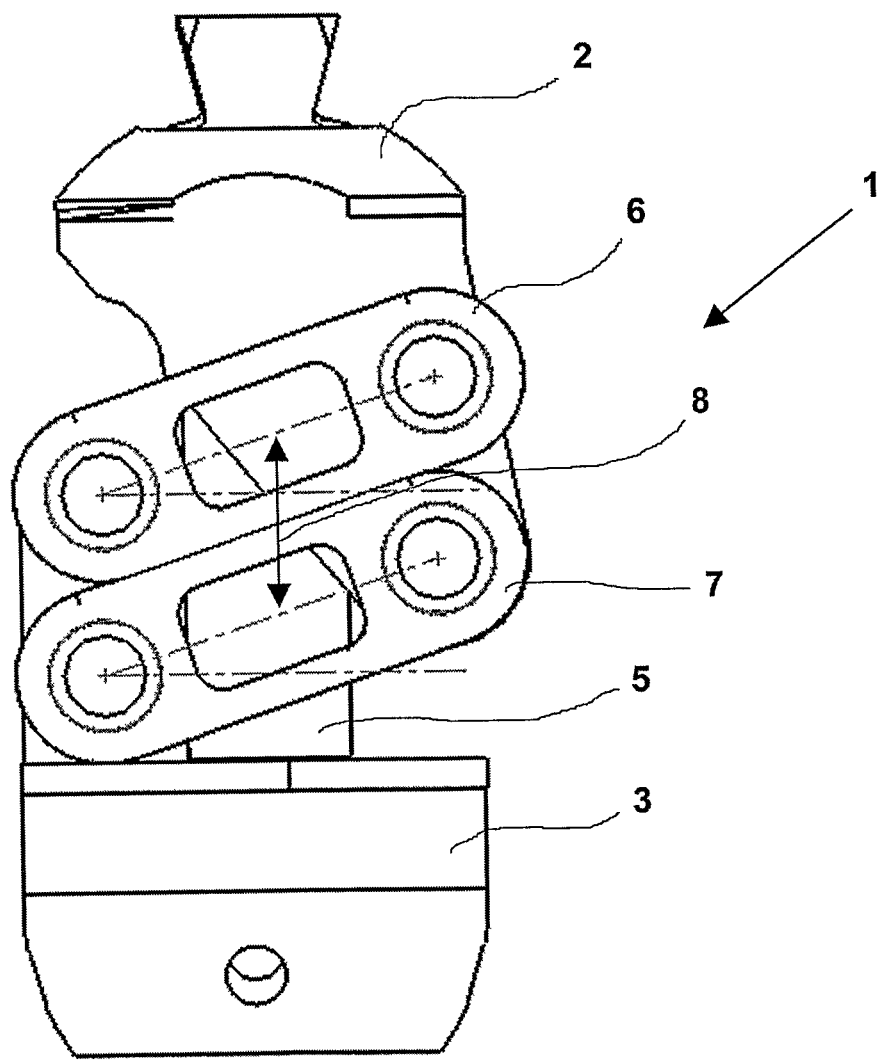
FIG. 3a is a side view of the damping device according to the invention in an unloaded condition.
Figure 3B:
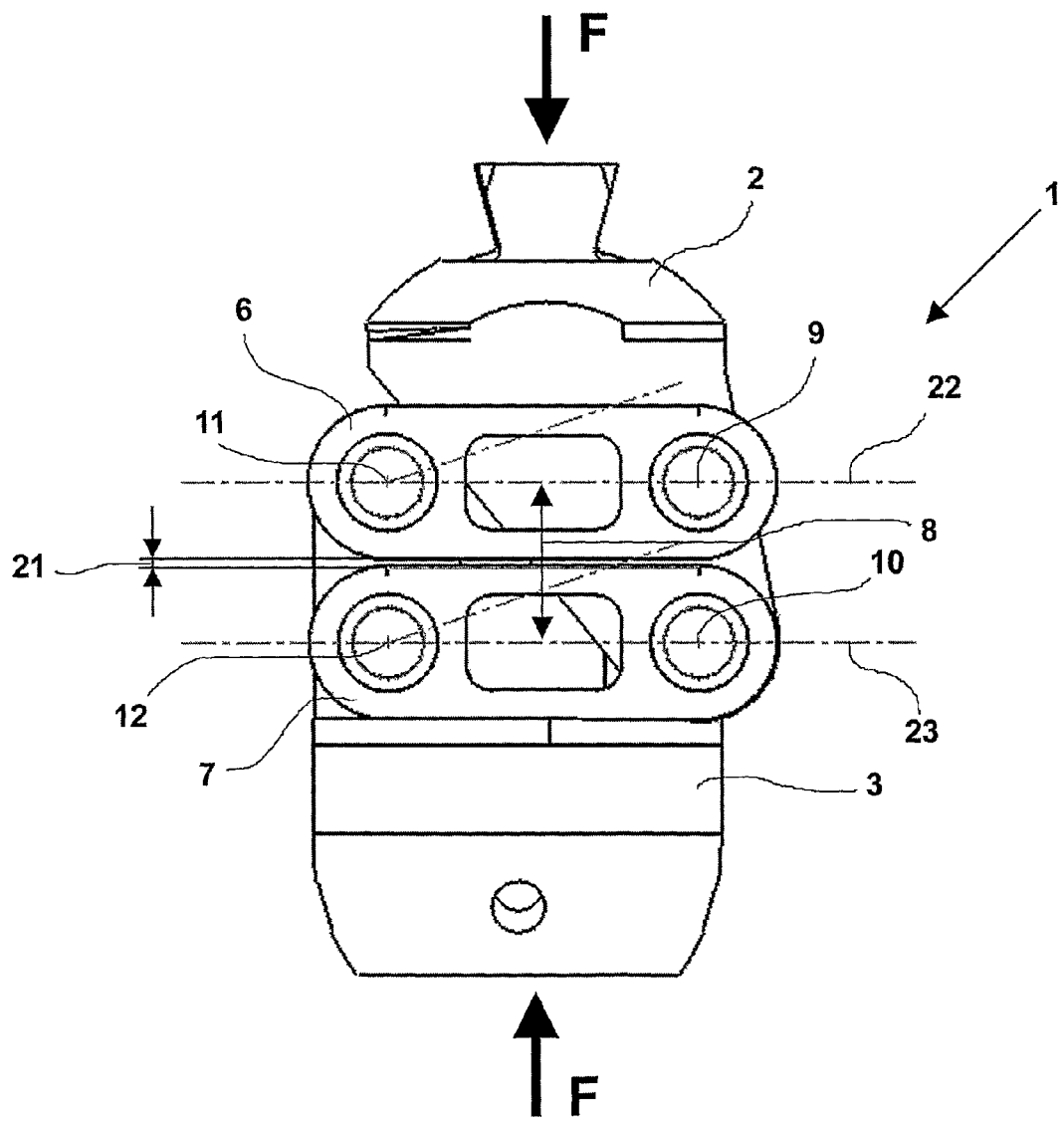
FIG. 3b is a view corresponding to FIG. 3a, showing the damping device in a loaded condition.

In FIGS. 3*a* and 3*b*, the damping device 1 is illustrated in an unloaded and a loaded condition, respectively. In this example, the second member 3 is imagined to have a fixed position. During vertical loading of the damping device 1 with a force F, the damping element 5 will be compressed and the first member 2 will be displaced along the main damping direction 8 (in reality along a curve segment, the radius of which being determined by the length and the relative location of the linkage arms 6, 7). During displacement of the first member 2 towards the second member 3, the first member 2 will maintain substantially the same orientation in relation to the second member 3 as in the unloaded condition. It should be observed, however, that the desired orientation could be substantially maintained even if the size and/or relative location of the linkage arms 6, 7 were not fully optimised. A certain compensation could namely be obtained by means of one or more of the pivoting centres of the linkage arms being slightly flexible due to the use of a type of bushing which allows a certain displacement of the pivoting centre in question.

As mentioned above, it is convenient that the two linkage arms 6, 7, being displaced simultaneously and substantially following each other during loading and unloading of the damping device 1, are arranged substantially adjacent to each other. By means of a suitable selection of a distance 21 (illustrated in FIG. 3*b*) between the linkage arms 6, 7, at least one extreme condition (illustrated in FIG. 3*a*) can be determined for the relative positions of the first 2 and the second 3 member, and thereby also the length of stroke of the damping device 1 can be indirectly determined.

As is illustrated in FIGS. 3*a* and 3*b*, the both linkage arms can be relatively arranged for abutting against each other, at a certain maximum distance (se FIGS. 2*a* and 3*a*) in the main damping direction 8 between the first member 2 and the second member 3, in order to prevent further pivoting of the linkage arms 6, 7 and relative displacement of the first member 2 and the second member 3 in a direction away from each other. During this condition, implying contact between said two linkage arms 6, 7 and locking against further pivoting of the linkage arms in an anti-clockwise direction, the damping element 5 can remain substantially unaffected, preferably non-compressed. Furthermore, at a certain minimum distance (see FIGS. 2*b* and 3*b*) in the main damping direction 8 between the first member 2 and the second member 3, substantially maximum influence can be exerted on the damping element 5, preferably compressed to a maximum extent. The distance which the first and the second member can move in a direction from each other (during unloading of the damping device) before the locked condition sets in will be a function of, among other things, the magnitude of the distance 21 between the two linkage arms 6, 7. The distance between the linkage arms 6, 7 will vary between zero and a maximum value. The maximum value occurs when the two geometrical axes of rotation 9, 11 and 10, 12, respectively, for one and the same linkage arm 6 and 7, respectively, are located on a geometrical line 22 and 23, respectively, being substantially perpendicular to the damping direction 8. The value zero is assumed in the locked condition, when the linkage arms 6, 7 are inclined to a maximum extent relative to the damping direction 8. In the illustrated example, this implies that a maximum distance 21 occurs between the linkage arms 6, 7 when the two linkage arms 6, 7 are arranged substantially horizontally and the damping element 5 is substantially compressed to a maximum extent. As is evident from FIG. 3*b*, the damping device 1 assumes a second extreme position when the lower linkage arm 7 abuts against the second member 3, which prevents further pivoting of the linkage arms 6, 7 in a clockwise direction. In the illustrated example, this extreme position coincides with the maximum distance 21 occurring between the linkage arms 6, 7.

Figures 4, 5:
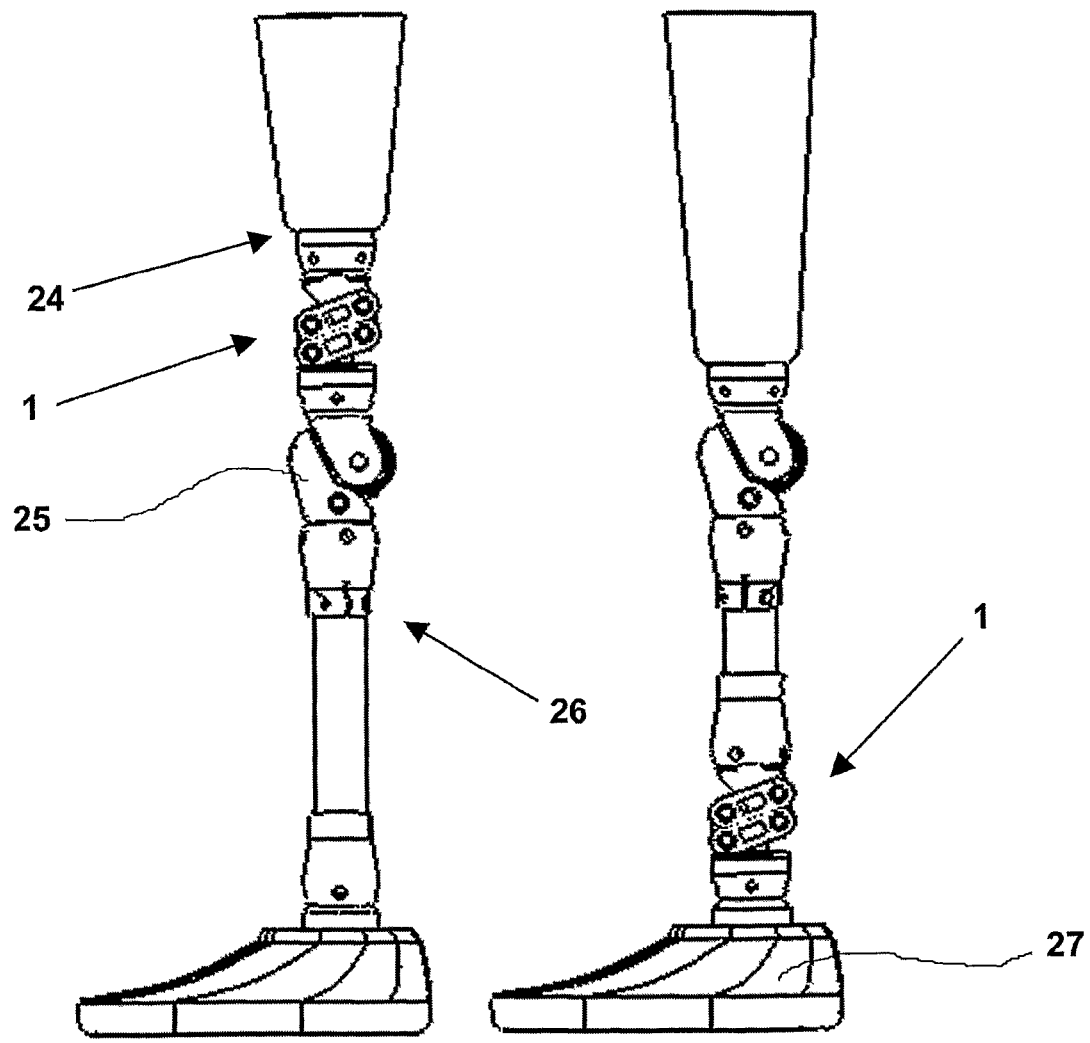
FIG. 4 is a leg prosthesis provided with a damping device according to the invention being arranged above the knee.
FIG. 5 is a leg prosthesis provided with a damping device according to the invention being arranged at the foot.

FIGS. 4 and 5 show two examples of locations for the damping device 1 according to the invention in a leg prosthesis. In FIG. 4, the damping device 1 is positioned above the knee joint 25 of a leg prosthesis 26, whereas the damping device 1 in FIG. 5 is positioned further below, closest to the foot 27. Besides providing vertical damping during a normal load condition, the damping device 1 in the embodiment being illustrated in FIG. 4 can also unload the anchorage position 24 where the leg prosthesis is attached to a user in case a user of the prosthesis 26 hits the knee against an object or loads the knee by kneeling down. Such an unloaded condition can be particularly advantageous in case the prosthesis is interconnected with the user via an implant. Also in the embodiment in FIG. 4, the relatively small mounting length of the damping device 1 according to the invention is advantageous, for example in the case when a user is amputated relatively close to the knee joint 25.

Figure 6:
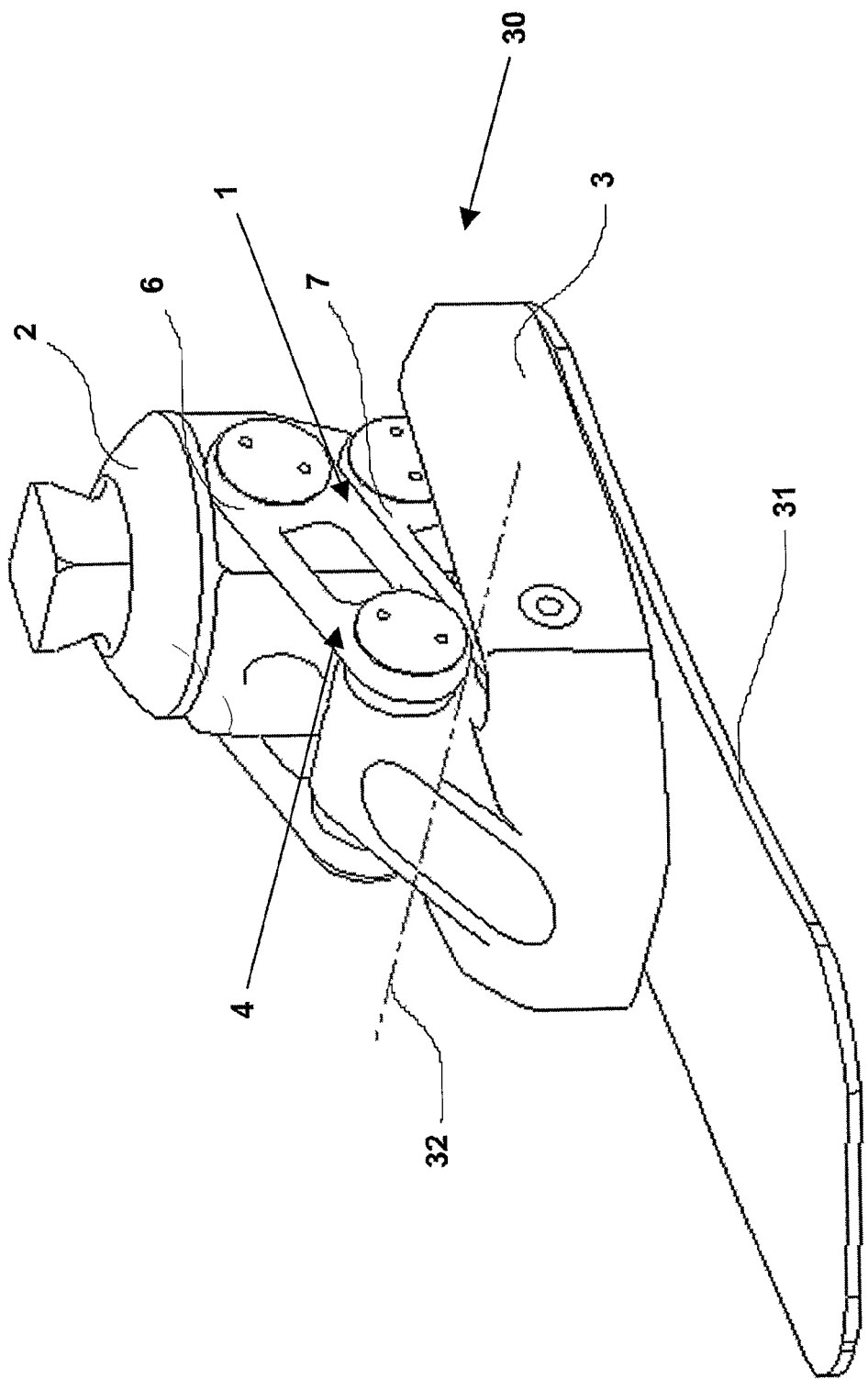
FIG. 6 is a perspective view of an artificial ankle joint including a damping device according to the invention.
Figure 7:
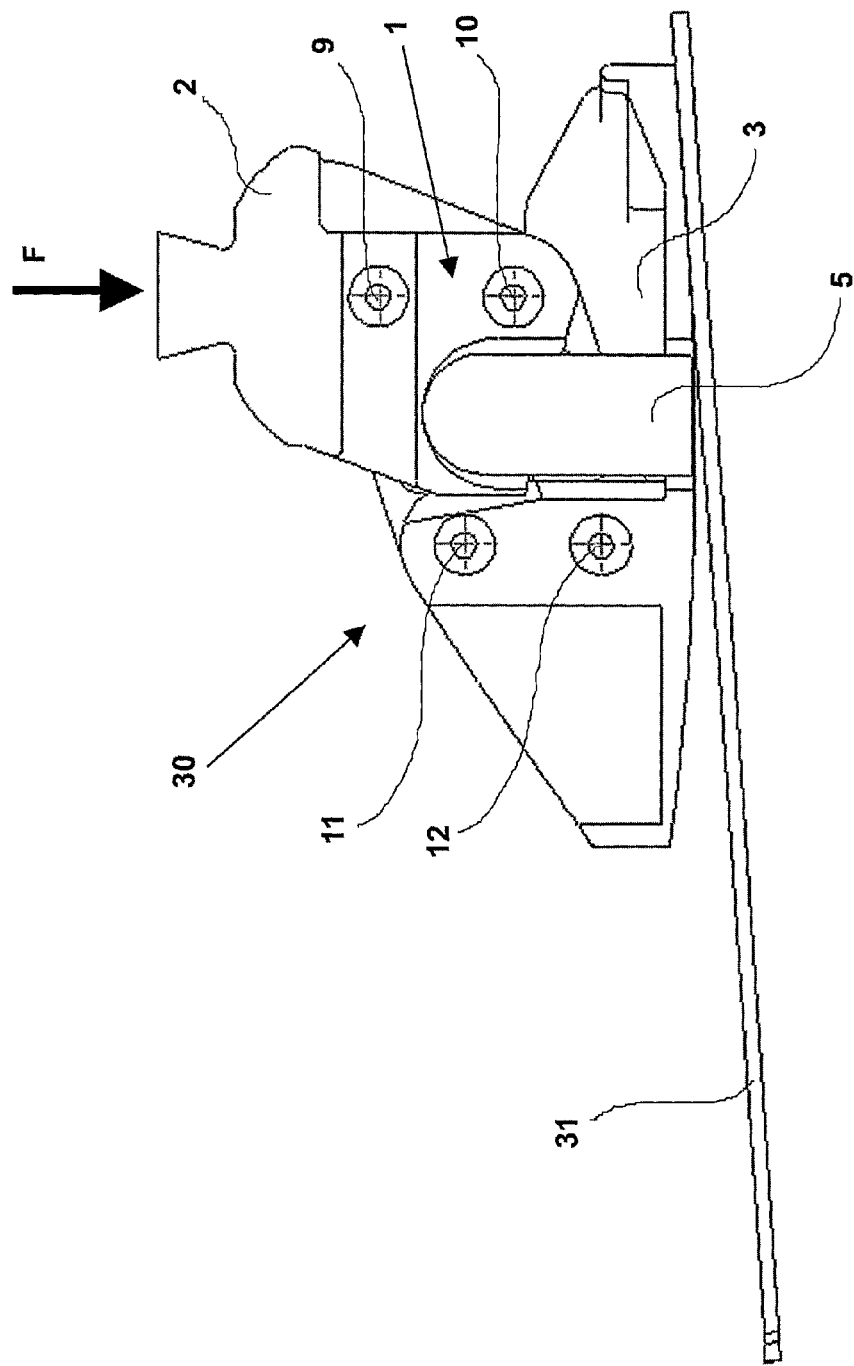
FIG. 7 is a sectional side view of the ankle joint being illustrated in FIG. 6.

In FIG. 6, a damping device 1 according to the invention is arranged in an artificial ankle joint 30 being illustrated in a perspective view. In FIG. 7, the ankle joint is illustrated in a sectional side view. In this embodiment, the damping device 1 according to the invention is used in order to form an artificial ankle joint 30 providing a substantially vertical damping when using the ankle joint prosthesis. This implies that the first member (hereinafter called the upper member) constitutes an upper member 2 for connection to a lower leg and the second member (hereinafter called the lower member) constitutes a lower member 3 for connection to a foot blade 31. It should be observed that the damping device 1 being arranged in the ankle joint 30 can exhibit all features of the damping device according to the invention which are described above for the general case. The coupling means 4 includes two sets of said two linkage arms 6, 7, both being pivotally arranged in relation to the upper member 2 and the lower member 3. It should be observed that the pivoting centre 32 of the ankle joint as a whole does not coincide with anyone of the geometrical axes of rotation 9, 10, 11, 12 of the linkage arms 6, 7, but is rather a function of the relative positions of the these axes of rotation.

The damping element 5 is arranged between the upper member 2 and the lower member 3 in order to counteract a relative movement between the upper 2 and the lower 3 member during vertical loading F of the prosthesis 30. In this way, a smooth, damped movement can be obtained during foot strike. Even if the damping device 1, during heel strike, could provide a certain damping also in the form of so-called plantar flexion of the foot blade 31 in relation to the upper member 2 and the lower leg (not shown), the main task of the damping element 5 is to counteract a relative movement between the upper member 2 and the lower member 3 during a substantially vertical loading F of the damping device 1, as described previously.

It will be appreciated that the present invention is not limited to the embodiments being described in the foregoing and illustrated in the drawings, rather, a person skilled in the art will discover that many modifications can be made within the scope of protection of the appended claims. For example when utilising an implant prosthesis, where the prosthesis is anchored by means of an implant in a skeletal part of a user, the damping device according to the invention could be used in different positions for shock-absorption with the purpose of preventing the prosthesis and/or the skeletal part from being damaged in such an implant prosthesis.

The invention claimed is:

1. A damping device for a prosthesis, comprising a first member for connection to a first component, a second member for connection to another component, and a means for coupling together the first member and the second member and for relative displacement of the first member and the second member, and a damping element which is arranged to counteract a relative displacement between the first member and the second member when loading the damping device, wherein the coupling means comprises first and second linkage arms, both being pivotally arranged in relation to the first member and the second member, wherein the first and second linkage arms are arranged at different positions with respect to a main damping direction of the damping device for substantially maintaining the relative orientations of the first member and the second member when loading the damping device, when the first member and the second member are displaced in relation to each other during pivoting of the first and second linkage arms and exertion of influence on the damping element:
wherein the first and second linkage arms each exhibit a first geometrical axis of rotation for relative pivoting of the first and second linkage arms and the first member, and a second geometrical axis of rotation for relative pivoting of the first and second linkage arms and the second member;
wherein said first geometrical axes of rotation, about which the first and second linkage arms and the first member are pivotable in relation to each other, are arranged at different positions along a first geometrical line that is substantially parallel to the main damping direction and move in a linear direction;
wherein said second geometrical axes of rotation, about which the first and second linkage arms and the second member are pivotable in relation to each other, are arranged at different positions along a second geometrical line that is substantially parallel to the main damping direction and move in a linear direction.

2. Damping device according to claim 1, wherein said first and second linkage arms are substantially of the same length and arranged substantially in parallel.

3. Damping device according to claim 1, wherein the first linkage arm is arranged above the second linkage arm for maintaining the relative orientations of the first member and the second member when damping in a substantially vertical direction.

4. Damping device according to claim 1, wherein the first and second linkage arms are arranged substantially adjacent to each other.

5. Damping device according to claim 1, wherein the damping element is arranged between the first member and the second member.

6. Damping device according to claim 1, wherein at least one of the first member and the second member is provided with a recess for accommodating the damping element.

7. Damping device according to claim 6, wherein the recess and the damping element are arranged such that a play is present between a limiting surface of the recess and the damping element in one or several directions that are substantially perpendicular to the main damping direction.

8. Damping device according to claim 1, wherein a maximum influence is exerted on the damping element at a minimum distance in the main damping direction between the first member and the second member.

9. Damping device according to claim 8, wherein said first and second linkage arms are arranged substantially perpendicularly in relation to the main damping direction and with a small relative distance in the main damping direction when the maximum influence is exerted on the damping element.

10. A damping device for a prosthesis, comprising a first member for connection to a first component, a second member for connection to another component, and a means for coupling together the first member and the second member and for relative displacement of the first member and the second member, and a damping element which is arranged to counteract a relative displacement between the first member and the second member when loading the damping device, wherein the coupling means comprises at least two linkage arms, both being pivotally arranged in relation to the first member and the second member, wherein the linkage arms are arranged at different positions with respect to a main damping direction of the damping device for substantially maintaining the relative orientations of the first member and the second member when loading the damping device, when the first member and the second member are displaced in relation to each other during pivoting of the linkage arms and exertion of influence on the damping element, wherein said two linkage arms are arranged to abut against each other, at a certain maximum distance in the main damping direction between the first member and the second member, in order to prevent further pivoting of the linkage arms and relative displacement of the first member and the second member in a direction away from each other.

11. Damping device according to claim 10, wherein the damping element remains substantially unaffected when said linkage arms abut against each other.

* * * * *